US012654014B2

(12) United States Patent
Rao

(10) Patent No.: US 12,654,014 B2
(45) Date of Patent: Jun. 16, 2026

(54) SYSTEMS AND METHODS BASED ON DEEP REINFORCEMENT LEARNING AND PLANNING FOR SHAPING NEURAL ACTIVITY, REWIRING NEURAL CIRCUITS, AUGMENTING NEURAL FUNCTION AND/OR RESTORING NEURAL FUNCTION

(71) Applicant: University of Washington, Seattle, WA (US)

(72) Inventor: Rajesh P.N. Rao, Seattle, WA (US)

(73) Assignee: University of Washington, Seattle, WA (US)

( * ) Notice: Subject to any disclaimer, the term of this patent is extended or adjusted under 35 U.S.C. 154(b) by 805 days.

(21) Appl. No.: 17/978,764

(22) Filed: Nov. 1, 2022

(65) Prior Publication Data

US 2023/0137595 A1 May 4, 2023

Related U.S. Application Data

(60) Provisional application No. 63/274,855, filed on Nov. 2, 2021.

(51) Int. Cl.
*A61N 1/36* (2006.01)
*A61N 1/02* (2006.01)
(Continued)

(52) U.S. Cl.
CPC ......... *A61N 1/36103* (2013.01); *A61N 1/025* (2013.01); *A61N 1/36135* (2013.01); *G06N 20/00* (2019.01); *G16H 40/63* (2018.01)

(58) Field of Classification Search
None
See application file for complete search history.

(56) References Cited

U.S. PATENT DOCUMENTS

2004/0131998 A1* 7/2004 Marom ................ A61N 1/3603
607/45
2007/0179534 A1* 8/2007 Firlik ................ A61M 5/14276
604/503

(Continued)

OTHER PUBLICATIONS

Berger , et al., "A Cortical Neural Prosthesis for Restoring and Enhancing Memory", Journal Neural Engineering, vol. 8 No. 4, Aug. 2011, 16 pages.

(Continued)

*Primary Examiner* — Mallika D Fairchild
(74) *Attorney, Agent, or Firm* — Dorsey & Whitney LLP

(57) ABSTRACT

Restoring and/or augmenting neural function may be achieved in some examples by receiving signals associated with a first region of a nervous system, and generating a stimulation pattern based on the signals associated with the first region of the nervous system and a first artificial network. The stimulation pattern may be provided to a second region of the nervous system to induce a behavioral output. In some examples, a second artificial network may be used to train the first artificial network. The second artificial network may be configured to predict the behavioral output from the individual based on the stimulation provided by the first artificial network. Parameters of the first artificial network can be adjusted using the output of the second artificial network to optimize the output signals of the first artificial network to achieve restoration and/or augmentation goals.

17 Claims, 6 Drawing Sheets

(51) Int. Cl.
 *G06N 20/00* (2019.01)
 *G16H 40/63* (2018.01)

(56) References Cited

U.S. PATENT DOCUMENTS

| | | | |
|---|---|---|---|
| 2018/0078770 A1* | 3/2018 | Rickert | A61N 1/37217 |
| 2019/0262612 A1 | 8/2019 | Rao et al. | |
| 2019/0299008 A1* | 10/2019 | Rao | G06N 3/084 |
| 2019/0321639 A1 | 10/2019 | Rao et al. | |

OTHER PUBLICATIONS

Jackson , et al., "Long-Term Motor Cortex Plasticity Induced by an Electronic Neural Implant", Nature vol. 444, pp. 56-60, Nov. 2006.

Moritz , et al., "Direct Control of Paralysed Muscles by Cortical Neurons", Nature vol. 456, Dec. 2008, pp. 639-642.

Rao , "Brain Co-Processors: Using AI to Restore and Augment Brain Function", Handbook of Neuroengineering, Jun. 2021, pp. 1-36.

Rao , "Brain-Computer Interfacing: An Introduction", Cambridge University Press, 2013, 351 pages.

Rao , "Towards Neural Co-Processors for the Brain: Combining Decoding and Encoding in Brain-Computer Interfaces", Current Opinion in Neurobiology, 2019, pp. 142-151.

* cited by examiner

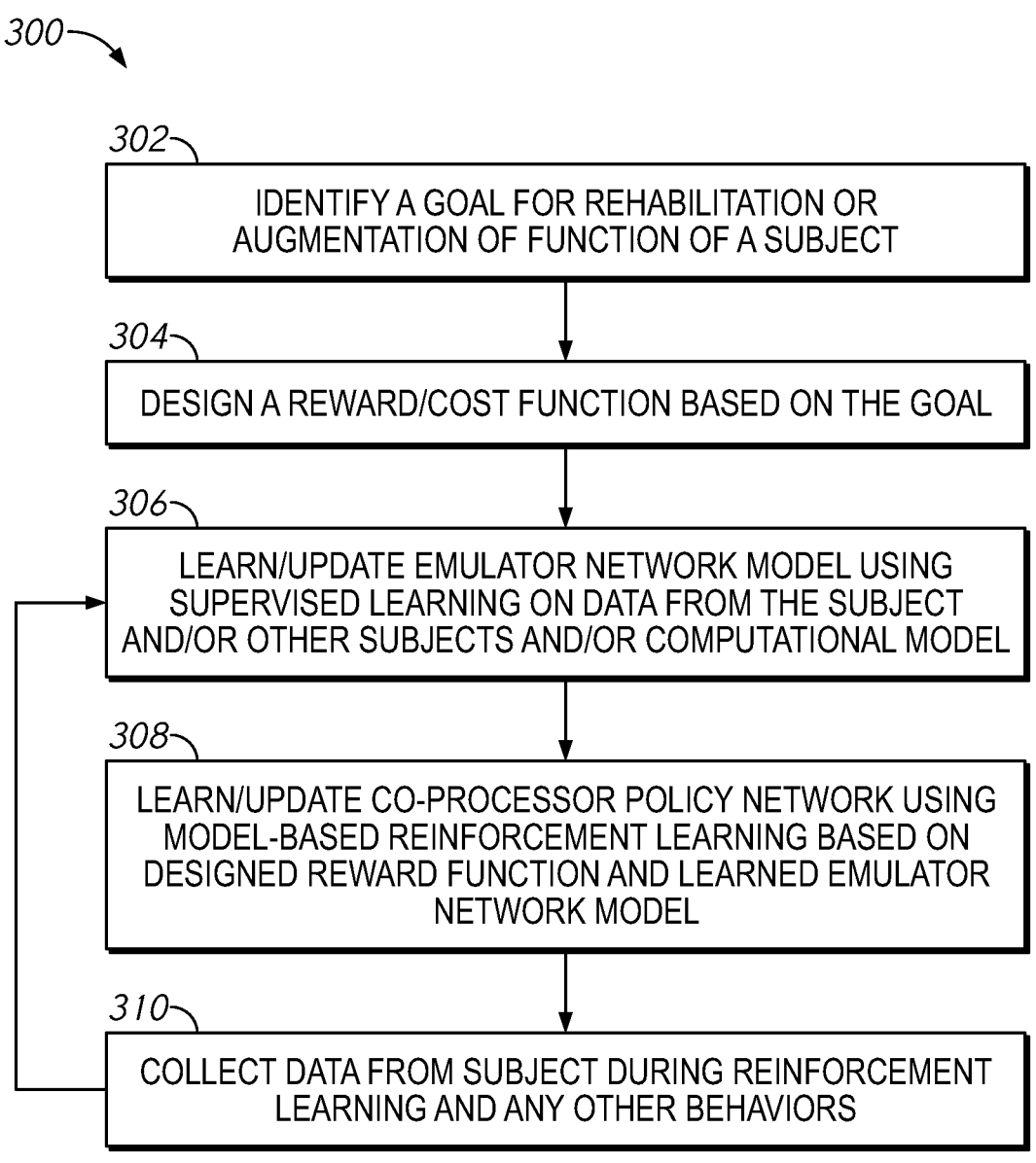

*300*

*302*
IDENTIFY A GOAL FOR REHABILITATION OR AUGMENTATION OF FUNCTION OF A SUBJECT

*304*
DESIGN A REWARD/COST FUNCTION BASED ON THE GOAL

*306*
LEARN/UPDATE EMULATOR NETWORK MODEL USING SUPERVISED LEARNING ON DATA FROM THE SUBJECT AND/OR OTHER SUBJECTS AND/OR COMPUTATIONAL MODEL

*308*
LEARN/UPDATE CO-PROCESSOR POLICY NETWORK USING MODEL-BASED REINFORCEMENT LEARNING BASED ON DESIGNED REWARD FUNCTION AND LEARNED EMULATOR NETWORK MODEL

*310*
COLLECT DATA FROM SUBJECT DURING REINFORCEMENT LEARNING AND ANY OTHER BEHAVIORS

*FIG. 3*

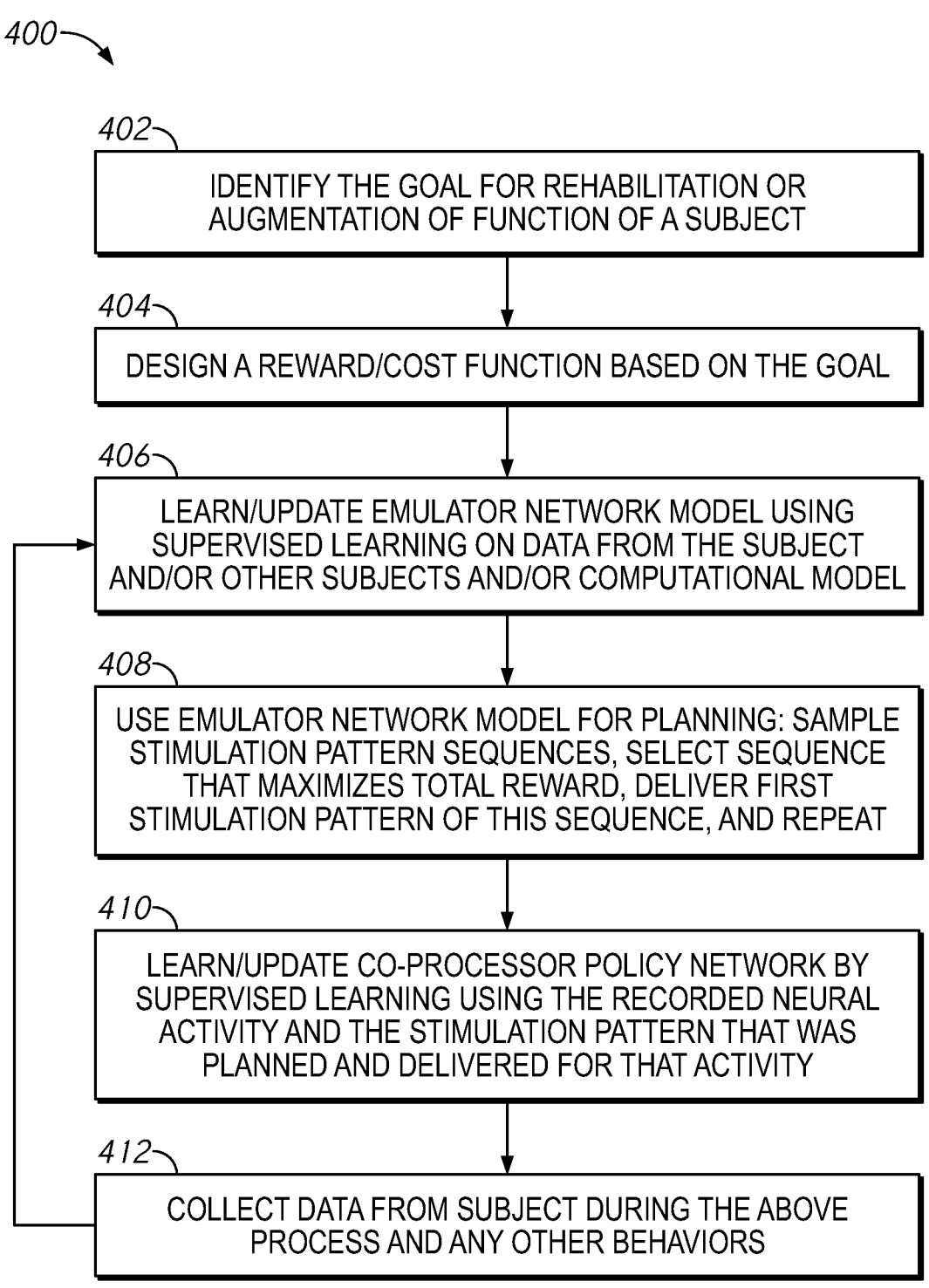

400

402
IDENTIFY THE GOAL FOR REHABILITATION OR AUGMENTATION OF FUNCTION OF A SUBJECT

404
DESIGN A REWARD/COST FUNCTION BASED ON THE GOAL

406
LEARN/UPDATE EMULATOR NETWORK MODEL USING SUPERVISED LEARNING ON DATA FROM THE SUBJECT AND/OR OTHER SUBJECTS AND/OR COMPUTATIONAL MODEL

408
USE EMULATOR NETWORK MODEL FOR PLANNING: SAMPLE STIMULATION PATTERN SEQUENCES, SELECT SEQUENCE THAT MAXIMIZES TOTAL REWARD, DELIVER FIRST STIMULATION PATTERN OF THIS SEQUENCE, AND REPEAT

410
LEARN/UPDATE CO-PROCESSOR POLICY NETWORK BY SUPERVISED LEARNING USING THE RECORDED NEURAL ACTIVITY AND THE STIMULATION PATTERN THAT WAS PLANNED AND DELIVERED FOR THAT ACTIVITY

412
COLLECT DATA FROM SUBJECT DURING THE ABOVE PROCESS AND ANY OTHER BEHAVIORS

IDENTIFY THE GOAL FOR REHABILITATION OR AUGMENTATION OF FUNCTION OF A SUBJECT

*504*

DESIGN A REWARD/COST FUNCTION BASED ON THE GOAL

*506*

LEARN/UPDATE CO-PROCESSOR POLICY NETWORK USING MODEL-FREE REINFORCEMENT LEARNING TO MAXIMIZE EXPECTED REWARD BASED ON DESIGNED REWARD FUNCTION

*508*

COLLECT DATA FROM SUBJECT DURING REINFORCEMENT LEARNING AND ANY OTHER BEHAVIORS

SYSTEMS AND METHODS BASED ON DEEP REINFORCEMENT LEARNING AND PLANNING FOR SHAPING NEURAL ACTIVITY, REWIRING NEURAL CIRCUITS, AUGMENTING NEURAL FUNCTION AND/OR RESTORING NEURAL FUNCTION

CROSS-REFERENCE TO RELATED APPLICATION

This application claims the filing benefit of U.S. Provisional Application No. 63/274,855, filed Nov. 2, 2021. This application is incorporated by reference herein in its entirety and for all purposes.

STATEMENT REGARDING FEDERALLY SPONSORED RESEARCH

This invention was made with government support under Grant No. EEC-1028725, awarded by the National Science Foundation. The government has certain rights in the invention.

BACKGROUND

The human brain is one of the world's most powerful autonomous computers. However, it remains a fragile organ that can be difficult to train and repair, and that is limited by the sensory inputs and processing capacity provided by the human body. The parallel functions of and the potential for connecting the brain and silicon computers have prompted considerable interest in the field of brain-computer interfaces. Brain-computer interfaces may be able to restore lost neurological function, address some of the limitations of the human brain as well as bolster our understanding of an organ with many functions and operations that remain to be understood. More specifically, the computational capabilities of biological neural networks and silicon computers are complementary. For example, human brains commonly transfer information bidirectionally with computers through normal sensory and motor channels. However, transferring information through direct recording of neural activity and electrical stimulation of brain sites is much more challenging. Nevertheless, recent advances in brain interface technologies, computing systems, and our understanding of the human brain have sparked new investigations into the brain-computer interfaces that directly record and/or stimulate the brain.

SUMMARY

The systems, methods, and apparatuses disclosed herein may use deep reinforcement learning and planning for shaping neural activity, rewiring neural circuits, augmenting neural function and/or restoring neural function. In some embodiments, the reinforcement learning may utilize a cost and/or reward function. In some embodiments, an artificial network used for generating instructions for stimulation patterns based on measured neural activities may be trained by another artificial network. The other artificial network may model a neural region or regions of the subject, and provide outputs of neural and behavioral states responsive to stimulation patterns.

According to at least one example of the disclosure, a model-free reinforcement learning method for augmenting or restoring neural function and inducing new neural connections in a nervous system of a human subject may include identifying a goal of augmentation or restoration of function of the subject, designing a reward function based on the goal, receiving neural activities generated by the subject in first neural regions of the subject, implementing, with a first machine learning algorithm a policy for mapping the neural activities in the first neural regions to stimulation patterns for second neural regions of the subject, based, at least in part, on the reward function.

According to at least one example of the disclosure, a system for augmenting or restoring neural function and inducing new neural connections in a nervous system of a human subject may include a processor configured to execute instructions, a non-transitory computer-readable medium encoded with instructions that when executed, cause the processor to implement a first machine learning algorithm configured to implement a policy for mapping neural activities in first neural regions to stimulation patterns for second neural regions of a subject, wherein the policy is based, at least in part, a reward function based on a goal of augmentation or restoration of function of the subject.

According to at least one example of the disclosure, a model-based reinforcement learning method and a model-based planning method for augmenting or restoring neural function and inducing new neural connections in a nervous system of a human subject may include identifying a goal of augmentation or restoration of function of the subject, designing a reward function based on the goal, implementing, with a first machine learning algorithm, a mapping between a plurality of sequences of stimulation patterns and a corresponding plurality of output neural and behavioral states, selecting, by planning with the mapping learned by the first machine learning algorithm, a sequence from the plurality of sequences of stimulation patterns that maximizes the reward, and training, using the mapping learned by the first machine learning algorithm, a second machine learning algorithm to implement a policy for mapping neural activities in first neural regions to the plurality of sequences of stimulation patterns for second neural regions of the subject, based, at least in part, on the reward function.

BRIEF DESCRIPTION OF THE DRAWINGS

FIG. 3 is a flowchart of a process or method for rehabilitation and/or augmentation of function of a subject with model-based reinforcement learning in accordance with embodiments of the present technology.

FIG. 4 is a flowchart of a process or method for rehabilitation and/or augmentation of function of a subject with model-based planning in accordance with embodiments of the present technology.

DETAILED DESCRIPTION

Figure 1:
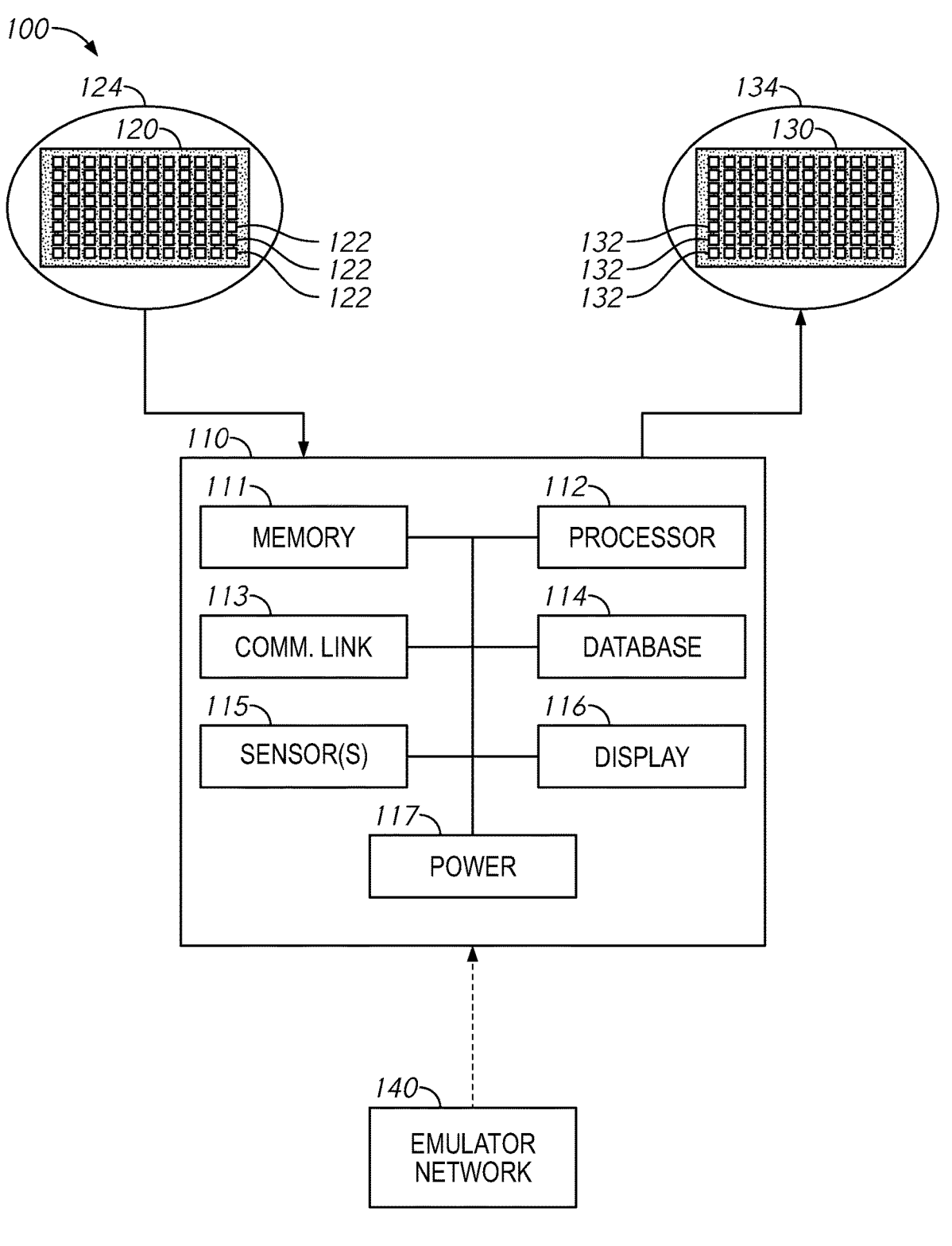
FIG. 1 is a partially schematic diagram of a system for augmenting neural function, restoring neural function, and/or inducing new neural connections in a nervous system of a subject configured in accordance with embodiments of the present technology.

A brain-computer interface (BCI) is a device that allows signals from the brain to be used to control devices such as prosthetics, cursors or robots, and in some cases, allows external signals to be fed back to the brain through neural stimulation. A special class of BCIs stimulate one region of the brain or nervous system based on neural activity in another region. This kind of a BCI, which can be referred to as a bi-directional BCI (BBCI), can be used to not only control devices or convey sensor information to the brain but also to induce plasticity, reanimate paralyzed limbs, and/or restore memory. A BBCI combined with artificial intelligence algorithms can be called a "brain co-processor."

In U.S. Pat. No. 11,083,895, which is incorporated herein by reference for any purpose, a method is described that includes receiving signals associated with a first region of the nervous system of the individual, and generating a stimulation pattern based on the signals associated with the first region of the nervous system and a first artificial network. The stimulation pattern may be output to a second region of the nervous system to induce a behavioral output from the individual and a second artificial network configured to predict the behavioral output from the individual. The induced behavioral output to the predicted behavioral output is compared to generate an error signal. Parameters of the first artificial network can be adjusted using the error signal and the second artificial network to optimize the stimulation patterns and other output signals to achieve restoration and/or augmentation goals. While an advance in the art, in some applications, an error signal is not available. In some of these applications, a different method may be used to optimize stimulation patterns and/or other output signals.

The present disclosure is directed generally toward a specific type of brain co-processor and associated methods for restoring, enhancing, and/or generating new neural function by adding new adaptive computational capabilities to the nervous system and/or inducing new neural connections in the nervous system (e.g., in the brain or spinal cord) of a subject. In several of the embodiments described below, a method for augmenting or restoring brain and nervous system function includes adaptively transforming neural signals received from one area to neural stimulation signals (e.g., stimulation patterns) to stimulate another area of the nervous system in order to achieve a desired functional outcome. The technique can use deep model-based or model-free reinforcement learning and/or planning to transform specific patterns of neural activity from an area being recorded and any external inputs into appropriate stimulation patterns in the same or different area in the nervous system and/or possible external outputs. The transformation may be designed to optimize total future expected reward/cost according to an arbitrary reward/cost function or reach particular neural or behavioral goal states. In some embodiments, no error signal is required to optimize the transformation (e.g., optimize one or more artificial networks used to generate stimulation pattern instructions based, at least in part, on neurological signal inputs).

By delivering appropriate activity-dependent stimulation patterns and solving the "temporal credit assignment" problem through reinforcement learning or planning, the method can be used for (i) steering neural activity to desirable future neural states and/or behavioral outcomes and (ii) promoting neuroplasticity between artificially connected neural regions, thereby rewiring brain regions and other regions of nervous system for achieving desired outcomes. The present technology can be used for both neuro-rehabilitation after neurological injury or disease, as well as for augmentation of natural human function.

In some embodiments, the present technology uses model-based or model-free reinforcement learning within a co-processor to learn a mapping ("policy") from input recordings to output stimulation patterns in a manner that optimizes a reward or cost function to achieve a desired outcome in augmentation or restoration of neural function. In other embodiments, the present technology uses model-based planning to plan a sequence of stimulation patterns and select the best next stimulation pattern(s) for optimizing the reward/cost function or reaching goal states. Such methods can be implemented as a co-processor with existing hardware for recording neural activity in the brain or nervous system, and any existing hardware for stimulating neural regions. Such technologies include, but are not limited to, electrical, optical, magnetic, and ultrasound-based recording and stimulation methods. The present technology can be implemented on processors implanted within the body, on an external computer, or using cloud computing via wireless communication with recording and stimulating systems within or worn on the body. In some examples, various methods or techniques may be implemented by encoding non-transitory computer-readable medium (or media) with processor-executable instructions. For example, one or more processors e.g., co-processors) may access the computer-readable medium and execute the instructions encoded therein. Execution of the instructions may implement some or all of the techniques disclosed herein (e.g., measure and store signals due to neural activity, generate stimulation patterns, cause stimulation patterns to be provided to a neural region, implement one or more artificial networks, train one or more neural networks, etc.).

Certain details are set forth in the following description and in FIGS. 1-6 to provide a thorough algorithmic understanding of various embodiments of the present technology. In other instances, well-known structures, materials, operations and/or systems often associated with neural stimulation and recording (e.g., hardware and methods for stimulating the nervous system of a subject and/or recording neural signals from the nervous system such as electrical, optical, magnetic, chemical, and ultrasound-based recording and stimulation methods) are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth.

The terminology used below is to be interpreted in its broadest reasonable manner, even though it is presented in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the disclosure.

Many of the details, dimensions, angles and other features shown in the Figures are merely illustrative of particular embodiments of the disclosure. Accordingly, other embodiments can have other details, dimensions, angles and features without departing from the spirit or scope of the present disclosure. In addition, those of ordinary skill in the art will appreciate that further embodiments of the disclosure can be practiced without several of the details described below.

I. SELECTED EMBODIMENTS OF SYSTEMS FOR AUGMENTING NEURAL FUNCTION, RESTORING NEURAL FUNCTION, AND/OR INDUCING NEW NEURAL CONNECTIONS IN A SUBJECT

The following discussion provides a general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, and/or a short-range radio network (e.g., via Bluetooth). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g., a Bluetooth network) on a propagated signal on a propagation medium (e.g., an electromagnetic wave(s) or a sound wave) over a period of time, or may be provided on any analog or digital network (e.g., packet switched, circuit switched, or other scheme).

FIG. 1 is a partially schematic diagram of a system 100 for augmenting neural function, restoring neural function, and/or inducing new neural connections in a nervous system of a subject (e.g., a human patient or able-bodied individual; not shown) configured in accordance with embodiments of the present technology. The system 100 includes a processing subsystem 110 configured to be communicatively/operably coupled to (i) a neural sensor module 120, (ii) a stimulation module 130, and (iii) optionally an emulator network module 140. An example of a suitable processing subsystem 110 is described in "The Neurochip-2: An Autonomous Head-Fixed Computer for Recording and Stimulating in Freely Behaving Monkeys," by Stavros Zanos, Andrew G. Richardson, Larry Shupe, Frank P. Miles, and Eberhard E. Fetz IEEE Transactions on Neural Systems And Rehabilitation Engineering, Vol. 19, No. 4, pg. 427-435, August 2011, which is also incorporated herein by reference in its entirety. An application of such a subsystem to induce neuroplasticity using a simple spike detection method is described in "Long-term motor cortex plasticity induced by an electronic neural implant," by Andrew Jackson, Jaideep Mavoori, and Eberhard E. Fetz, Nature, Vol. 444, pg. 56-60, Nov. 2, 2006, which is also incorporated herein by reference in its entirety.

The neural sensor module 120 is configured to detect neural signals (e.g., neuroelectrical activity, neurochemical activity) in the nervous system of the subject. In some embodiments, the neural sensor module 120 is implanted in and/or worn externally proximate to a region of interest 124 of the brain of the subject. The neural region of interest 124 can be, for example, a region of the subject's brain or another portion of the subject's nervous system. In some embodiments, the neural sensor module 120 can be a multi-channel sensor that includes a plurality of individual sensor elements 122 configured to detect one or more signals generated at different locations in and/or on the region of interest 124. For example, the sensor elements 122 can be configured to provide a spatial and/or spatiotemporal sampling of neural signals generated over the region of interest 124. More specifically, the sensor elements 122 can be configured to detect one or more of spikes, firing rates, local field potentials, optical or blood-oxygen level dependent (BOLD) activity, electroencephalogram (EEG) or electrocorticographic (ECoG) oscillatory features such as alpha waves, beta waves, gamma waves, and the like. In some embodiments, the sensor elements 122 can be ECoG electrodes that are configured to record ECoG features (e.g., beta waves) at the brain surface. In some embodiments, the number of individual sensor elements 122 (e.g., measurement channels) in the neural sensor module 120 can be selected to correspond to a characteristic of the region of interest 124 (e.g., the physical structure of the region, the degrees of freedom in a detectable signal at the region, the numbers of neurons in the region).

The stimulation module 130 is configured to be positioned at or proximate to a stimulation region 134 of the nervous system of the subject (e.g., the brain or spinal cord). The stimulation module 130 can be implanted in and/or worn externally by the subject, and can include any invasive or non-invasive hardware for stimulating the stimulation region 134. For example, the stimulation module 130 can be configured to stimulate the stimulation region 134 using one or more of: electrical activation, optical/optogenetic activation, magnetic activation, ultrasonic activation, and chemical activation. In some embodiments, the stimulation module 130 is a multi-channel module that includes a plurality of individual stimulating elements 132. Each of the stimulating elements 132 can be configured to stimulate a different location in and/or on the stimulation region 134, and to provide spatially and/or spatiotemporally differing stimulation patterns in and/or on the stimulation region 134. In some embodiments, the number of individual stimulating elements 132 (e.g., stimulation channels) in the stimulation module 130 can be selected to correspond to a characteristic (e.g., the physical structure) of the stimulation region 134. In some embodiments, the stimulation elements 132 can be ECoG electrodes that are configured to stimulate the surface of the brain of the subject. In such embodiments, the stimulation module 130 can be implanted within the subject proximate to the brain surface.

The emulator network module 140 (the "model") can be a computing device (or included in a computing device) separate from the processing subsystem 110 and/or integrated into the processing subsystem 110. The emulator network module 140 may include a memory, a processor, and/or other components for implementing the computing device. The emulator network module 140 can implement a machine learning and/or other algorithm (collectively referred to as an artificial network) for predicting neural activity and/or subject behavior induced by certain stimulation patterns. That is, for example, the emulator network module 140 acts as a "model" of the underlying neural system or behavior that can predict neural activity patterns and/or other behavior of the subject that would be induced by particular stimulation patterns delivered by the stimulation module 130. The emulator network module 140 may be trained based on data from the subject. For example, known stimulation patterns may be provided to a neural region of the subject, and the subsequent neural state of the same and/or different regions may be recorded. These sets of inputs and outputs may be provided as a training set to train the artificial network of the emulator network module 140. In some embodiments, the artificial network of the emulator network module 140 may be trained based on data from multiple neural regions of the subject (e.g., transfer learning) and/or data from multiple subjects. The artificial network may be implemented by one or more processors of the emulator network module 140 executing instructions, which may be stored in a non-transitory computer readable medium of the emulator network module 140.

The processing subsystem 110 comprises several components including memory 111 (e.g., one or more computer readable storage modules, mediums, components, devices) and one or more processors 112. The memory 111 can be configured to store information (e.g., signal data, subject information or profiles, environmental data, data collected from one or more sensors, media files) and/or executable instructions that can be executed by the one or more processors 112. The memory 111 can include, for example, instructions for (i) processing data from the neural sensor module 120, the emulator network module 140, and/or other sensors or sources, and (ii) generating stimulation patterns for output to the stimulation module 130 (e.g., based on a trained machine learning and/or other algorithm). The processing subsystem 110 can also include a communication link 113 (e.g., a wired communication link and/or a wireless communication link (e.g., Bluetooth, Wi-Fi, infrared, and/or another wireless radio transmission network)) and a database 114 configured to store data (e.g., signal data acquired from a region of interest, equations, filters) used in the techniques for promoting plasticity and/or enhancing neural activity, connectivity, and/or outflow for restoring or augmenting neural function, as disclosed herein.

One or more sensors 115 can provide additional data for use in restoring function in the subject. The sensors 115 can also provide other data pertinent to a condition and/or environment of the subject. For example, the sensors 115 may include one or more electrodes, ECoG or other neural sensors, voltammetry sensors of neurochemicals, blood pressure monitors, galvanometers, accelerometers, thermometers, hygrometers, blood pressure sensors, altimeters, gyroscopes, magnetometers, proximity sensors, barometers, microphones, cameras, Global Positioning System (GPS) sensors, Near Field Communication (NFC) sensors, etc. The sensors 115 can also be configured to provide information about the system 100 itself, such as an operating condition (e.g., power level, noise level, etc.) of any or all of the components included therein. One or more displays 116 can provide video output and/or graphical representations of data obtained by the system 100. The one or more displays 116 and/or other components of the processing subsystem 110 can include one or more input devices (e.g., buttons, touchscreens, keyboards, mice, joysticks, number pads) for receiving user input. A power supply 117 (e.g., a power cable, one or more batteries, and/or one more capacitors) can provide electrical power to components of the processing subsystem 110 and/or the system 100. In embodiments that include one or more batteries (e.g., where the system 100 is a portable system), the power supply 117 can be configured to recharge, for example, via a power cable, inductive charging, and/or another suitable recharging method.

In some embodiments, the processing subsystem 110 can include one or more components partially or wholly incorporated into the neural sensor module 120, the stimulation module 130, and/or the emulator network module 140. In other embodiments, however, the processing subsystem 110 may include components remote from the neural sensor module 120, the stimulation module 120, and/or the emulator network module 140, and connected thereto by a communication network (e.g., the Internet and/or another network or cloud computers). In some embodiments, for example, at least a portion of the processing subsystem 110 may reside on a mobile device (e.g., a mobile phone, a tablet, a personal digital assistant) and/or a computer (e.g., a desktop computer, a laptop) communicatively coupled to the neural sensor module 120, the stimulation module 130, and/or the emulator network module 140. Moreover, the processing subsystem 110 can be configured to be worn by the subject (e.g., carried by their body) and/or implanted in their body (e.g., in, on or proximate a region of their nervous system). More generally, the system 100 can be made sufficiently small to be worn externally and/or implanted in the subject and operate autonomously during hours of free and/or controlled behavior.

In some embodiments, the emulator network module 140 may be used to train an artificial network (e.g., a machine learning and/or other algorithm) implemented by the processing subsystem 110. In some embodiments, the artificial neural network may be implemented by one or more of the processors 112. In some embodiments, the one or more of the processors 112 may execute instructions stored in the memory 111 to implement the artificial neural network.

As noted, the emulator network module 140 may include a model of the neural system with which the processing subsystem 110 will be used. The processing subsystem 110 may receive signals associated with neurological activity as inputs and provide instructions for stimulation patterns as outputs. The stimulation patterns may be based, at least in part, on the received signals. During training, rather than providing the instructions for stimulation patterns to the stimulation module 130, the instructions for stimulation patterns may be provided as an input to the emulator network module 140. The emulator network module 140 model (which may also be an artificial network) may output an expected neurological state based, at least in part, on the instructions for stimulation patterns. The emulator network module 140 may determine whether the neurological state is desired or undesired based on previous training. In some embodiments, the emulator network module 140 may provide a score on a scale (e.g., 0-1, 0-100, −100-+100, etc.) based on the desirability and/or undesirability of the neurological state. This score may be provided to the processing subsystem 110, which may adjust the weights, architecture, and/or other parameters of the artificial network implemented by the processing subsystem 110. The training process of artificial network generating instructions for stimulation patterns based on signals and receiving feedback from the emulator network module 140 may continue until artificial network of the processing subsystem 110 has been optimized. The optimization may be based on a function, such as a reward and/or cost function. For example, a reward function may be maximized and/or a cost function may be minimized.

In some embodiments, once the artificial network implemented by the processing subsystem 110 has been trained, the processing subsystem may provide the instructions for neural stimulations to the stimulation module 130 in addition to or instead of the emulator network module 140. In some embodiments, the artificial network implemented by the processing system may be periodically retrained with the emulator network module 140 (e.g., once a day, once a week, once a month). In some embodiments, the emulator network module 140 may be periodically retrained as well. In some embodiments, the artificial networks of the emulator network module 140 and the processing subsystem 110 may have a same architecture e.g., both may be deep recurrent neural networks), but in other embodiments, the artificial networks may have different structures from one another (e.g., one may be a transformer neural network and the other may be a recurrent neural network).

II. SELECTED EMBODIMENTS OF METHODS FOR AUGMENTING NEURAL FUNCTION, RESTORING NEURAL FUNCTION, AND/OR INDUCING NEW NEURAL CONNECTIONS IN A SUBJECT

Figure 2:
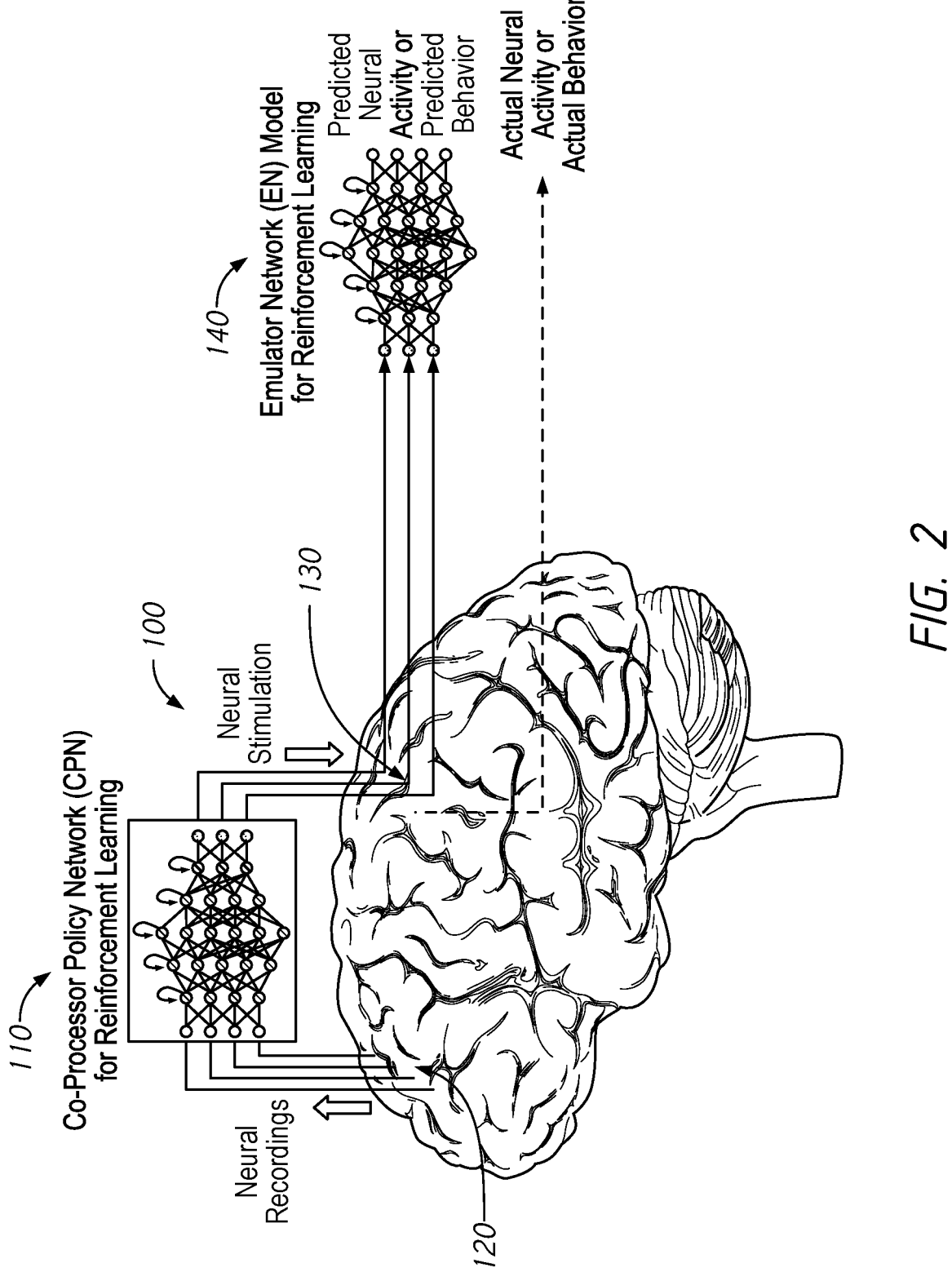
FIG. 2 is a partially schematic view of the system of FIG. 1 showing neural network components for restoring/augmenting neural function and promoting neuroplasticity in a brain of a subject in accordance with embodiments of the present technology.

FIG. 2 is a partially schematic view of the system 100 of FIG. 1 for promoting neuroplasticity in, for example, a brain of a subject in accordance with embodiments of the present technology. In some embodiments, the system 100 can be implemented as a co-processor for the brain or the nervous system in general. In the illustrated embodiments, the input for the system 100 consists of spatiotemporal recordings of neural activity in the brain or nervous system, Deep reinforcement learning can be used to train a deep artificial neural network—called a co-processor policy network (CPN)—which learns an optimal "policy" mapping between input neural activity patterns in one set of regions (and optionally external inputs from sensors, the interact, and the like) to output stimulation patterns in the same or other regions (and optionally, control outputs for external actuators). The policy is optimal in terms of optimizing reward and/or cost for example, maximizing the total expected future reward as defined by an artificially-engineered reward function or by measuring natural reward signals such as dopamine in the brain. Accordingly, the reinforcement learning method can solve the temporal credit assignment problem that is, favoring actions (stimulation patterns and control outputs) that lead to desirable neural states and outputs in the future.

In some embodiments, the reward/cost function can be designed or selected to associate different rewards or costs with different neural activity patterns, reward signals in the brain, and/or behavioral/task states. Using model-free or model-based reinforcement learning algorithms such as Q-learning, temporal difference (TD), and/or actor-critic learning, the CPN can be trained to learn a policy that maximizes total expected future reward.

In some embodiments, for model-based reinforcement learning, an emulator network (EN; e.g., the emulator network module 140 of FIG. 1) can be trained to predict the neural activity, reward signals, and/or behavior elicited by different stimulation patterns. The EN can then be used as a model for learning the policy using model-based reinforcement learning. That is, the EN can generate mappings of simulation patterns to output behaviors or signals that can be used to train the CPN. Model-based reinforcement learning reduces the number of training trials compared to model-free reinforcement learning. This may be advantageous in some applications as the high number of repeated neural stimulations required to train the CPN may take up a significant amount of the subject's time, cause physical or mental discomfort, and/or increase risk of brain damage. Accordingly, in some applications, model-based reinforcement learning techniques, such as those that utilize an emulator network, such as emulator network module 140 may be preferable.

In some embodiments, for model-based planning, an emulator network (EN; e.g., the emulator network module 140 of FIG. 1) can be trained to predict the neural activity, reward signals, and/or behavior elicited by different sequences of stimulation patterns. The EN can then be used for planning by the CPN: at each step, a number of candidate sequences of stimulation patterns ("actions") can be provided by the CPN and their consequences (predicted neural activity or behavior) can be generated using the EN. Each sequence can be evaluated according to the reward/cost function, and the best sequence selected. The first "action" (stimulation pattern) can be selected and used as the output of the CPN, for example, as a form of model-predictive control, Additionally, each selected stimulation pattern at a time step and the corresponding input to the CPN can be used to train the CPN policy such that in the future, the input can be mapped directly to the stimulation pattern instead of planning.

In some embodiments, the CPN and/or the EN may include deep recurrent neural networks. In some embodiments, using a recurrent neural network may give the CPN "memory" as to the last input signal and/or stimulation pattern instruction provided. This may allow the CPN to "plan" by selecting sequences of stimulations based on received neural activity signals in some embodiments. In some applications, the memory of the CPN may prevent the CPN from repeatedly providing a same stimulation pattern instruction for a same input signal. For example, when the input neurological activity signals indicates a subject wants to pick up an object, the CPN may provide a stimulation pattern instruction (or instructions) to achieve the goal of picking up the object. However, the neurological activity signals may not immediately change after the stimulation pattern instruction has been provided. A recurrent neural network may prevent the CPN from sending the same stimulation pattern instruction again because the CPN "remembers" the instructions have already been sent. In some embodiments, the CPN and/or the EN may include a transformer network, which may also provide "memory" capabilities.

FIG. 3 is a flowchart of a process or method for rehabilitation and/or augmentation of function of a subject with model-based reinforcement learning in accordance with embodiments of the present technology. The method shown in flowchart 300 may be performed in whole or in part by system 100 shown in FIG. 1 in some embodiments. In some embodiments, the method shown in flowchart 300 may be performed in whole or in part by processing subsystem 110 and emulator network module 140.

At block 302, the method includes identifying one or more goals for rehabilitation and/or augmentation of function of a subject. In some embodiments, the goal may alternatively or additionally include restoration of function (e.g., neural function) of the subject. For example, the goal can be restoring a movement of the subject, such as reaching toward an object after a paralyzing injury. In other embodiments, the goal can be to improve/restore other modalities and other types of function such as, for example, mapping inputs from a memory-related area (and/or an external information source) to another memory area to facilitate or restore access to particular memories (e.g., in memory loss) or to unlearn traumatic memories (e.g., in PTSD), mapping inputs from one sensory area (and/or an external sensor) to another sensory area to restore or augment sensation and perception, connecting areas involved in emotion processing to augment or rehabilitate emotional function, and/or augmenting the brain's knowledge, skills, information processing, and learning capacities with artificial intelligence based on artificial neural networks and reinforcement learning that combine neural recording and stimulation with external information from novel sensors or information sources such as the Internet and commands to external actuators.

At block 304, the method includes designing a reward and/or cost function based on the goal. In embodiments with multiple goals, each goal may have its own reward and/or cost function. In other embodiments with multiple goals, the goals may share a reward and/or cost function. In some embodiments, the function may associate high reward scores with desirable behavioral or brain states. In some embodiments, the function can also or alternatively associate costs, such as a negative penalty for each stimulation pattern, with undesirable behavioral or brain states to encourage the policy to use fewer stimulations to achieve the goal.

At block 306, the method includes training an emulator network to model an appropriate neurological region(s) of the subject using reinforcement learning or other training technique. In some embodiments, supervised learning may be used to train the emulator network. The emulator network may be trained with data including stimulation patterns as inputs and resulting neurological states as outputs. The stimulation patterns may be based on stimulations provided to one or more neural regions, and the neurological states may be states measured at one or more neural regions, which may be the same or different than the stimulated regions. In some embodiments, data from the subject may be used to train the emulator network. In some embodiments, data from other subjects may be used instead of or in addition to the data from the subject. In some embodiments, data from a computational model may be used in addition to or instead of data from the subject(s). In some embodiments, the method may further include collecting the data from the subject and/or subjects. For example, the subject may be asked to voluntarily generate different neural activities in first neural regions A, B, C, . . . ("source areas") for mapping to the different target responses. For example, the subject can voluntarily generate the different neural activities by making a movement or imagining making a movement, and the resulting neural response can be recorded in the first neural regions A, B, C, . . . .

In some embodiments, the emulator network may include a deep recurrent neural network M to model the effects of stimulation by learning a mapping between input stimulation patterns in the second regions D, E, F, . . . (potentially overlapping with A, B, C, . . . ) and output brain states or behavioral states and rewards to apply model-based reinforcement learning. Alternately, if endogenous neural activity in the second neural regions D, E, F, . . . also elicits behavioral or goal-related brain states, the network M can be trained to learn a mapping between neural activity in region D, E, F, . . . and the output behavioral or brain states and rewards. Then, the network can be used as a model of the effects of stimulation on behavioral or brain states and rewards, and the method shown in flowchart 300 can employ a model-based reinforcement learning technique such as actor-critic learning or model-based planning to select stimulation patterns and learn a policy based on the learned model to map neural activity patterns in first neural regions A, B, C, . . . to stimulation patterns in the second neural regions D, E, F, . . . (potentially overlapping with A, B, C, . . . ) that optimize the expected reward.

At block 308, the method includes training a CPN to generate instructions for stimulation patterns based on neural activity signals using reinforcement learning or other training technique. In some embodiments, during training, the CPN may be provided with neurological activity signals, and stimulation pattern instructions generated by the CPN may be provided to the emulator network. Based on the stimulation pattern instructions received from the CPN, the emulator network may output a neurological state. The neurological state may be assigned a value based on the reward and/or cost function. The neurological state and/or value generated by the function may be provided to the CPN to adjust weights and/or other parameters of the CPN. The process of the CPN providing outputs to the emulator network, and the emulator network providing feedback to the CPN may be repeated until a reward of the reward function is maximized and/or a cost of the cost function is minimized. In some embodiments, when multiple goals each have different functions, the process may be repeated for each function. In some embodiments, the functions may be used in parallel to train the CPN. In these embodiments, absolute maximums or minimums for each function may not be reached, but a collective minimum or maximum may be achieved across the functions (e.g., compromise between competing tasks/goals).

After training, the CPN may be "deployed" in the subject to assist with rehabilitation and/or augmentation of function. Optionally, at block 310 the method may further include collecting data from the subject during deployment. Data may include neurological activity signals from one or more neural regions, resulting states in one or more neural regions responsive to stimulation patterns provided by the stimulator module 130 (e.g., responsive to instructions provided by the CPN). The collected data may be provided back to the emulator network to further train and/or retrain the emulator network as shown by the arrow connecting block 310 and 306. The CPN may then be further trained and/or retrained with the updated emulator network. In some embodiments, the data collected at block 310 may periodically be provided to the emulator network (e.g., hourly, daily, weekly), and the emulator network and CPN may subsequently be retrained periodically.

FIG. 4 is a flowchart of a process or method for rehabilitation and/or augmentation of function of a subject with model-based planning in accordance with embodiments of the present technology. The method shown in flowchart 400 may be performed in whole or in part by system 100 shown in FIG. 1 in some embodiments. In some embodiments, the method shown in flowchart 400 may be performed in Whole or in part by processing subsystem 110 and emulator network module 140.

At block 402, the method includes identifying one or more goals for rehabilitation and/or augmentation of function of a subject. In some embodiments, the goal may alternatively or additionally include restoration of function (e.g., neural function) of the subject. For example, the goal can be restoring a movement of the subject, such as reaching toward an object after a paralyzing injury. In other embodiments, the goal can be to improve/restore other modalities and other types of function such as, for example, mapping inputs from a memory-related area (and/or an external information source) to another memory area to facilitate or restore access to particular memories (e.g., in memory loss) or to unlearn traumatic memories (e.g., in PTSD), mapping inputs from one sensory area (and/or an external sensor) to another sensory area to restore or augment sensation and perception, connecting areas involved in emotion processing to augment or rehabilitate emotional function, and/or augmenting the brain's knowledge, skills, information processing, and learning capacities with artificial intelligence based on artificial neural networks and reinforcement learning that combine neural recording and stimulation with external information from novel sensors or information sources such as the Internet and commands to external actuators.

At block 404, the method includes designing a reward and/or cost function based on the goal. In embodiments with multiple goals, each goal may have its own reward and/or cost function. In other embodiments with multiple goals, the goals may share a reward and/or cost function. In some embodiments, the function may associate high reward scores with desirable behavioral or brain states. In some embodiments, the function can also or alternatively associate costs, such as a negative penalty for each stimulation pattern, with undesirable behavioral or brain states to encourage the policy to use fewer stimulations to achieve the goal.

At block 406, the method includes training an emulator network to model an appropriate neurological region(s) of the subject using reinforcement learning or other training technique. In some embodiments, supervised learning may be used to train the emulator network. The emulator network may be trained with data including stimulation patterns as inputs and resulting neurological states as outputs. The stimulation patterns may be based on stimulations provided to one or more neural regions, and the neurological states may be states measured at one or more neural regions, which may be the same or different than the stimulated regions. In some embodiments, data from the subject may be used to train the emulator network. In some embodiments, data from other subjects may be used instead of or in addition to the data from the subject. In some embodiments, data from a computational model may be used in addition to or instead of data from the subject(s). In some embodiments, the method may further include collecting the data from the subject and/or subjects. For example, the subject may be asked to voluntarily generate different neural activities in first neural regions A, B, C, . . . ("source areas") for mapping to the different target responses. For example, the subject can voluntarily generate the different neural activities by making a movement or imagining making a movement, and the resulting neural response can be recorded in the first neural regions A, B, C, . . . .

At block 408, the method may include using the emulator network for planning. Planning may include providing sample stimulation pattern sequences (e.g., a sequence of multiple stimulation patterns) and selecting a sequence that maximizes a total reward based on the output of the emulator network, delivering a first stimulation pattern of the sequence to the input of the emulator network, and repeating.

At block 410, the method includes training a CPN with supervised learning to generate instructions for stimulation pattern sequences (and optionally also stimulation patterns) based on the recorded neural activity signals and the stimulation pattern sequences that were planned and delivered for that activity. In some embodiments, during training, the stimulation pattern instructions generated by the CPN may be provided to the emulator network. Based on the sequence of stimulation pattern instructions received from the CPN, the emulator network may output a neurological state. The neurological state may be assigned a value based on the reward and/or cost function. The neurological state and/or value generated by the function may be provided to the CPN to adjust weights and/or other parameters of the CPN. The process of the CPN providing outputs to the emulator network, and the emulator network providing feedback to the CPN may be repeated until the total reward based on the reward function is maximized and/or total cost based on the cost function is minimized. In some embodiments, when multiple goals each have different functions, the process may be repeated for each function. In some embodiments, the functions may be used in parallel to train the CPN. In these embodiments, absolute maximums or minimums for each function may not be reached, but a collective minimum or maximum may be achieved across the functions.

After training, the CPN may be "deployed" in the subject to assist with rehabilitation and/or augmentation of function. Optionally, at block 412 the method may further include collecting data from the subject during deployment, Data may include neurological activity signals from one or more neural regions, resulting states in one or more neural regions or behavioral states generated in response to sequences of stimulation patterns (and/or individual stimulation patterns) provided by the stimulator module 130 (e.g., responsive to instructions provided by the CPN). The collected data may be provided back to the emulator network to further train and/or retrain the emulator network as shown by the arrow connecting block 412 and 406. The CPN may then be further trained and/or retrained with the updated emulator network. In some embodiments, the data collected at block 412 may periodically be provided to the emulator network (e.g., hourly, daily, weekly), and the emulator network and CPN may subsequently be retrained periodically.

Figure 5:
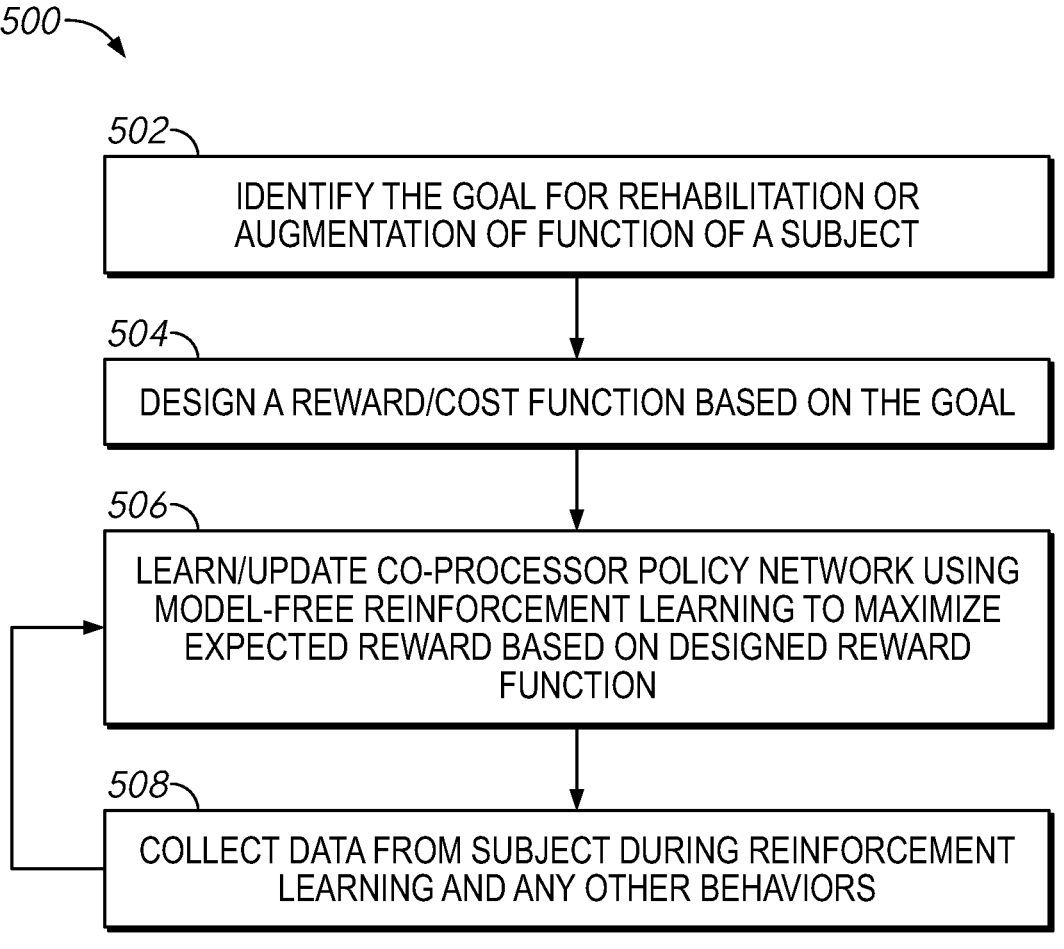
FIG. 5 is a flowchart of a process or method for rehabilitation and/or augmentation of function of a subject with model-free reinforcement learning in accordance with embodiments of the present technology.

FIG. 5 is a flowchart of a process or method for rehabilitation and/or augmentation of function of a subject with model-free reinforcement learning in accordance with embodiments of the present technology. The method shown in flowchart 500 may be performed in whole or in part by system 100 shown in FIG. 1 in some embodiments. In some embodiments, the method shown in flowchart 500 may be performed in whole or in part by processing subsystem 110 and emulator network module 140.

At block 502, the method includes identifying one or more goals for rehabilitation and/or augmentation of function of a subject. In some embodiments, the goal may alternatively or additionally include restoration of function (e.g., neural function) of the subject. For example, the goal can be restoring a movement of the subject, such as reaching toward an object after a paralyzing injury. In other embodiments, the goal can be to improve/restore other modalities and other types of function such as, for example, mapping inputs from a memory-related area (and/or an external information source) to another memory area to facilitate or restore access to particular memories (e.g., in memory loss) or to unlearn traumatic memories (e.g., in PTSD), mapping inputs from one sensory area (and/or an external sensor) to another sensory area to restore or augment sensation and perception, connecting areas involved in emotion processing to augment or rehabilitate emotional function, and/or augmenting the brain's knowledge, skills, information processing, and learning capacities with artificial intelligence based on artificial neural networks and reinforcement learning that combine neural recording and stimulation with external information from novel sensors or information sources such as the Internet and commands to external actuators.

At block 504, the method includes designing a reward and/or cost function based on the goal. In embodiments with multiple goals, each goal may have its own reward and/or cost function. In other embodiments with multiple goals, the goals may share a reward and/or cost function. In some embodiments, the function may associate high reward scores with desirable behavioral or brain states. In some embodiments, the function can also or alternatively associate costs, such as a negative penalty for each stimulation pattern, with undesirable behavioral or brain states to encourage the policy to use fewer stimulations to achieve the goal.

At block 506, the method includes training and/or updating the CPN using model-free reinforcement learning. The training may maximize the reward and/or minimize the cost functions. At block 508, the method includes collecting data from the subject during the reinforcement learning and/or any other behaviors. The data may include signals of electrical neurological activity, brain states, dopamine levels, and/or other signals. Some or all of the signals may be responsive to stimulations provided to the subject by the stimulation module 130 based on instructions provided by the CPN. The data may be associated with values based on the reward and/or cost function(s). The data and the values may be provided back to the CPN as indicated by the arrow connecting blocks 508 and 506. The data and values may be used to adjust the weights and/or other parameters of the CPN.

In some embodiments, the feedback from block 508 may be provided to block 506 to continuously train the CPN. In some embodiments, the feedback from block 508 may be provided to block 506 until a reward is maximized and/or a cost is minimized. In some of these embodiments, the training of the CPN may be repeated periodically (e.g., hourly, daily, weekly).

As noted, in some embodiments, the CPN includes a machine learning algorithm, such as a deep recurrent neural network or transformer network N, to learn a policy for mapping the neural activities in the first neural regions A, B, C, . . . along with any external inputs to stimulation patterns for second neural regions D, E, F, . . . (which may include one or more of A, B, C, . . . ) along with any external outputs by applying the model-free reinforcement learning. The external inputs may be option and may include inputs from sensors 115. In some embodiments, block 508 can include recording the resulting behavioral or brain state and associated reward, and Q-learning or TD-learning may be used at block 506 to update the policy.

Figure 6:
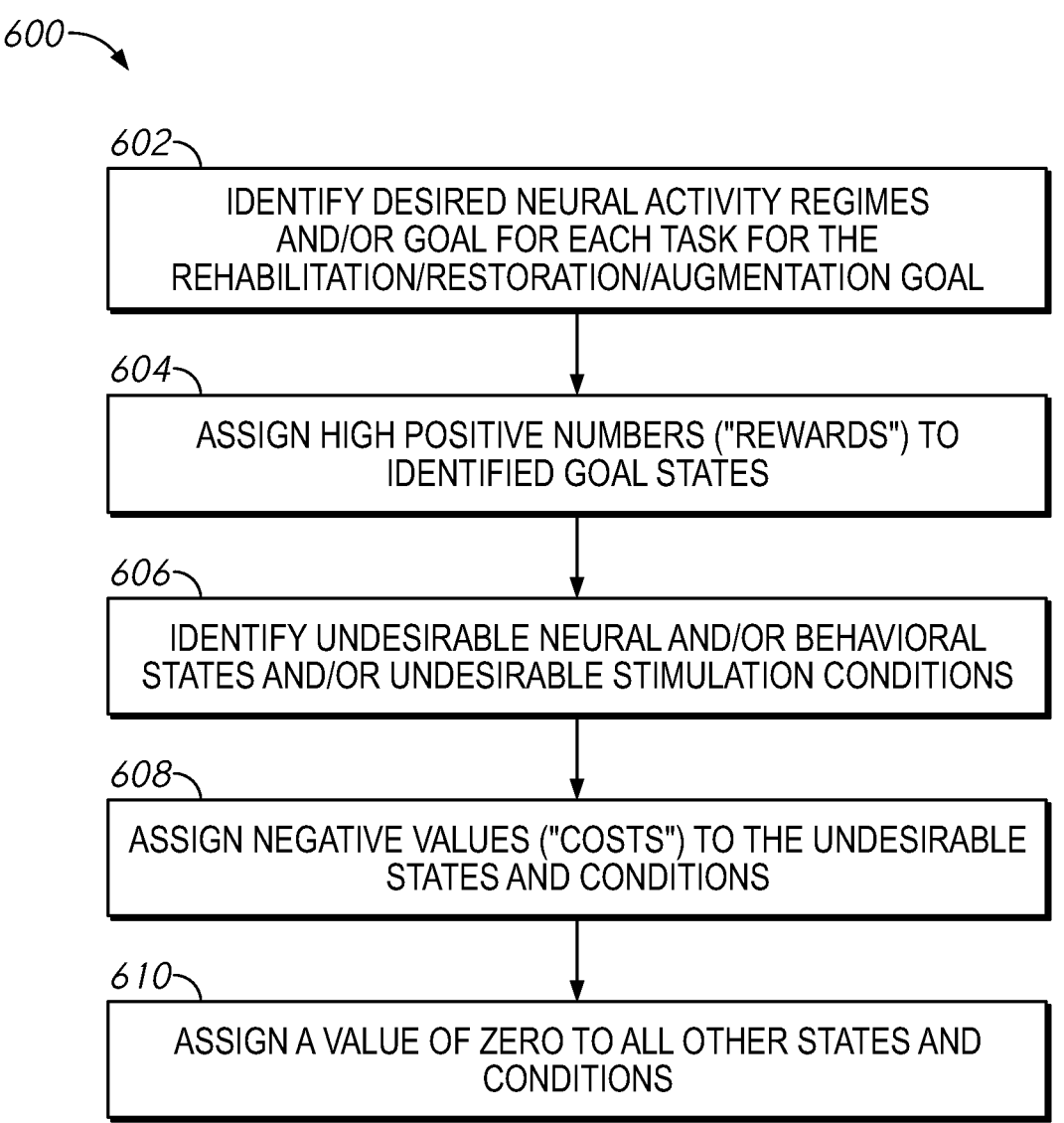
FIG. 6 is a flowchart of a process or method for designing a reward and/or cost function in accordance with embodiments of the present technology.

FIG. 6 is a flowchart of a process or method for designing a reward and/or cost function in accordance with embodiments of the present technology. The method shown in flowchart 600 may be performed in whole or in part by system 100 shown in FIG. 1 in some embodiments. In some embodiments, the method shown in flowchart 600 may be performed in whole or in part by a computing system coupled to the system 100. In some embodiments, the process or method for designing the reward and/or cost function shown in flowchart 600 may be used by one or more of the methods or processes shown in FIGS. 3-5. The method illustrated in flowchart 600 is provided merely as an example, and other suitable techniques for designing a reward and/or cost function may be used in other embodiments.

At block 602, the method may include identifying desired neural activity regimes and/or goals for each task of the rehabilitation, restoration, and/or augmentation goal(s). In other words, what neural activity or neural state is associated with successful completion of a task associated with the goal. For example, when the overall goal is restoring movement of a subject, neural activity regimes and/or goals for multiple tasks associated with the goal may be determined. For example, the neural activity associated with successfully taking a step forward with a left foot and/or the neural activity associated with successfully taking a step forward with a right foot. The neural states may be identified by collecting data from one or more subjects asked to perform, attempt to perform, and/or imagine performing the tasks.

At block 604, the method may include assigning high positive numbers (e.g., rewards) to identified goal states. For example, high positive numbers may be assigned to neural activity recorded when the subject successfully took a step.

At block 606, the method may include identifying neutral and/or undesirable neural states, behavioral states, and/or undesirable stimulation conditions. In other words, what neural activity or neural state is associated with unsuccessful completion of a task associated with the goal. Continuing the example above, the neural activity associated with unsuccessfully taking a step with either food may be identified. Examples of undesirable stimulation conditions may include providing multiple stimulations (e.g., it may be desirable to achieve the goal with the fewest number of stimulations and/or lowest voltage and/or current level of stimulation).

At block 608, the method may include assigning negative values (e.g., costs) to the undesirable neural and/or behavioral states and/or stimulation conditions. At block 610, the method may include assigning zero values to all other (e.g., neutral) states and conditions.

Any or all of the methods or processes described with reference to FIGS. 3-6 may be performed, at least in part, by one or more processors executing instructions stored on a non-transitory computer-readable medium.

The various states and conditions and their assigned values may define, at least in part, the reward and/or cost function for the task(s) associated with the goal. When a stimulation pattern generated by instructions from a CPN results in a neural state or condition, the value associated with the state or condition may be determined and provided back to the CPN. The value may be used to adjust the weights and/or other parameters of the CPN to maximize the reward and/or minimize the cost.

The artificial pathways created by the trained CPN can promote neuroplasticity between the connected regions, leading to neural enhancement, neural augmentation, and/or targeted-rehabilitation of function. The embodiment illustrated in FIG. 2 shows the application of the present technology to the brain, but the present technology can be applied to any set of neural regions for example, from the brain to the spinal cord for restoring function or rehabilitation after spinal cord injury.

Accordingly, in some aspects of the present technology a CPN trained by reinforcement learning or planning can process neural inputs and transform each input to an optimal output stimulation pattern intended to maximize total future expected reward according to a task-specific or behavior-specific reward function. After training, stimulation patterns produced by the reinforcement learning policy (via the CPN) can cause a desired response such as a movement or speech, a sensory percept, or even abstract thoughts, memories or feelings. The present technology can be used to restore a lost sensory, motor, and/or cognitive function after injury or disease, or to augment the brain and nervous system with a new function, new sensor or motor capabilities, or new cognitive capabilities. By repeatedly pairing patterns of inputs with patterns of output stimulation, the CPN promotes neuroplasticity between connected regions via biological mechanisms such as Hebbian plasticity. As a result, in some cases, the co-processor may eventually be no longer required after a period of use and may be removed once function is restored or augmented to a satisfactory level.

In some aspects of the present technology, the methods and systems can rewire neural circuits of the subject. That is, the present technology prescribes a reinforcement learning mechanism in which subsets of neurons in a neural region Y are adaptively stimulated whenever particular subsets of neurons get activated in a region X in order to achieve desired goals through a reward/cost function. If there are existing connections from region X to region Y, the present technology can strengthen (or weaken) these connections due to the natural phenomenon of neuroplasticity—for example, Hebbian plasticity or spike-timing dependent plasticity (STDP). By adaptively delivering appropriate stimulation patterns based on the subject's responses, the present technology promotes rewiring of the connections between X and Y to achieve subject-specific goals.

After a sufficient amount of coupling between regions X and Y using the methods and systems of the present technology, neurons in region X will automatically be able to recruit neurons in region Y to achieve a desired response (such as a particular grasp movement or augmentative response). At this stage, the co-processor implementing the methods of the present technology may no longer be required and can therefore be removed once function is restored or augmented to a satisfactory level.

III. CONCLUSION

The systems, methods, and apparatuses disclosed herein may use deep reinforcement learning and planning for shaping neural activity, rewiring neural circuits, augmenting neural function and/or restoring neural function. In some applications, the use of a cost and/or reward function for reinforcement learning and planning may allow for training artificial networks when error functions are unavailable or difficult to obtain. In some embodiments, an artificial network used for generating instructions for stimulation patterns based on measured neural activities may be trained by another artificial network. The artificial network may model a neural region or regions or behavior of the subject. In some applications, using one artificial network to train another artificial network may reduce or eliminate the need for repeated brain stimulation of the subject or subjects. In some applications, this may reduce the risk of brain injuries or discomfort of the subject.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments (e.g., the disclosed system may include components for simultaneous augmentation and restoration of function in a nervous system of a subject).

Moreover, unless the word or is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method for augmenting or restoring neural function and inducing new neural connections in a nervous system of a human subject, the method comprising:
   identifying a goal of augmentation or restoration of function of the subject;
   designing a reward function based on the goal;
   receiving neural activities generated by the subject in first neural regions of the subject;
   implementing, with a first-machine learning algorithm, a policy for mapping the neural activities in the first neural regions to stimulation patterns for second neural regions of the subject, based, at least in part, on the reward function;
   providing, from the machine learning algorithm, stimulation instructions based on the policy; and
   providing stimulation patterns to the second neural regions of the subject based on the stimulation instructions.

2. The method of claim 1, wherein the machine learning algorithm is a first machine learning algorithm, and further comprising:
   training the first machine learning algorithm with a second machine learning algorithm that models effects of stimulation by learning a mapping between input stimulation patterns in the second neural regions and (a) output states of a brain of the subject or behavioral states of the subject and (b) rewards.

3. The method of claim 2, wherein the training comprises:
   providing the stimulation patterns for the second neural regions from the first machine learning algorithm to the first machine learning algorithm;
   providing the rewards from the second machine learning algorithm to the first machine learning algorithm; and
   adjusting the policy based, at least in part, on the rewards.

4. The method of claim 1, wherein the first machine learning algorithm comprises a deep recurrent neural network.

5. The method of claim 1, further comprising:
   training the first machine learning algorithm, wherein the training comprises:

measuring the neural activities generated by the subject in the first neural regions;

providing a plurality of known stimulations to the second neural regions;

measuring a corresponding plurality of brain states of the subject responsive to the plurality of known stimulations;

assign a reward to each of the plurality of brain states; and adjusting the policy based, at least in part, on the rewards.

6. The method of claim 1, further comprising:

training the first machine learning algorithm, wherein the training comprises:

measuring the neural activities generated by a plurality of other subjects in the first neural regions;

providing a plurality of known stimulations to the second neural regions of the plurality of other subjects;

measuring a corresponding plurality of brain states of the plurality of other subjects responsive to the plurality of known stimulations;

assign a reward to each of the plurality of brain states; and adjusting the policy based, at least in part, on the rewards.

7. The method of claim 1, further comprising:

receiving external inputs from sensors or other information sources, wherein the first machine learning algorithm implements the policy for mapping the neural activities in the first neural regions and the inputs from the sensors to the stimulation patterns for the second neural regions of the subject and outputs to the sensors.

8. The method of claim 1, wherein the stimulation patterns comprise sequences of stimulation patterns.

9. A system for augmenting or restoring neural function and inducing new neural connections in a nervous system of a human subject, the system comprising:

a processor configured to execute instructions;

a non-transitory computer-readable medium encoded with instructions that when executed, cause the processor to implement a first machine learning algorithm configured to implement a policy for mapping neural activities in first neural regions to stimulation patterns for second neural regions of a subject, wherein the policy is based, at least in part, a reward function based on a goal of augmentation or restoration of function of the subject; and a stimulation module, wherein the stimulation module is configured to provide the stimulation patterns to the second neural regions of the subject.

10. The system of claim 9, further comprising a sensor configured to receive an input, wherein the mapping is further based on the input received by the sensor.

11. The system of claim 9, further comprising a computing device configured to implement a second machine learning algorithm configured to model effects of stimulation by learning a mapping between input stimulation patterns in the second neural regions and (a) output states of a brain of the subject or behavioral states of the subject and (b)

rewards, wherein the computing device is communicatively coupled to the processor, wherein the instructions when executed further cause the processor to use the second machine learning algorithm to train the first machine learning algorithm.

12. The system of claim 9, further comprising a neural sensor module configured to sense the neural activities in the first neural regions of the subject.

13. A method for augmenting or restoring neural function and inducing new neural connections in a nervous system of a human subject, the method comprising:

identifying a goal of augmentation or restoration of function of the subject;

designing a reward function based on the goal;

implementing, with a first machine learning algorithm, a mapping between a plurality of sequences of stimulation patterns and a corresponding plurality of neural states;

selecting, with the first machine learning algorithm, a sequence of the plurality of sequences of stimulation patterns that maximizes the reward;

training, with the first machine learning algorithm, a second machine learning algorithm to implement a policy for mapping neural activities in first neural regions to the plurality of sequences of stimulation patterns for second neural regions of the subject, based, at least in part, on the reward function;

providing, with the second machine learning algorithm, stimulation instructions based on the policy; and providing stimulation patterns to the second neural regions of the subject based on the stimulation instructions.

14. The method of claim 13, further comprising:

receiving neural activities generated by the subject in first neural regions of the subject;

and generating, with the second machine learning algorithm, the stimulation instructions for the sequence of the plurality of sequences of stimulation patterns that maximizes the reward.

15. The method of claim 13, further comprising:

receiving neural activities generated by the subject in first neural regions of the subject;

receiving a neural state of the subject responsive to a stimulation; and retraining the first machine learning algorithm based, at least in part, on the neural activities and the neural state.

16. The method of claim 15, further comprising retraining the second machine learning algorithm after retraining the first machine learning algorithm.

17. The method of claim 13, wherein designing the reward function comprises:

identifying neural activities for a task of the goal;

assigning positive numbers to identified neural activities associated with desirable states or successful completion of the task; and assigning negative numbers to identified neural activities associated with undesirable states or unsuccessful completion of the task.

* * * * *